United States Patent [19]

Schmitt et al.

[11] 4,189,478
[45] Feb. 19, 1980

[54] MEDICINAL COMPOSITION AND ITS USE AS ANTIDEPRESSIVE AGENT

[75] Inventors: Karl Schmitt; Irmgard Hoffmann, Both of Bad Soden am Taunus; Werner Fülberth, Kelkheim; Willi Stammberger, Hofheim am Taunus, all of Fed. Rep. of Germany

[73] Assignee: Hoechst Aktiengesellschaft, Frankfurt, Fed. Rep. of Germany

[21] Appl. No.: 910,782

[22] Filed: May 30, 1978

[30] Foreign Application Priority Data

Jun. 1, 1977 [DE] Fed. Rep. of Germany ....... 2724683

[51] Int. Cl.² ..................... A61K 31/33; A61K 31/47
[52] U.S. Cl. ..................................... 424/244; 424/258
[58] Field of Search ................................. 424/244, 258

[56] References Cited

U.S. PATENT DOCUMENTS 3,577,424  5/1971  Ehrhart et al. ...................... 424/250

OTHER PUBLICATIONS

Chem. Abst., 85-14126h (1976).
Chem. Abst., 85-14128Q (1976).
Chem. Abst., 85-14109J (1976).

*Primary Examiner*—Stanley J. Friedman
*Attorney, Agent, or Firm*—Curtis, Morris & Safford

[57] ABSTRACT

What is disclosed are medicinal compositions, useful as anti-depressive agents, containing a compound of the formula;

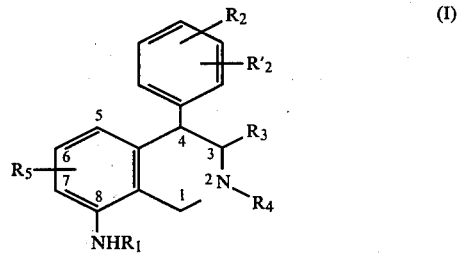

in which $R_1$, $R_3$ and $R_4$, which may be identical or different, and represent hydrogen atoms or lower alkyl or aralkyl groups, and $R_2$ and $R_2'$, which may be identical or different, represent hydrogen or halogen atoms, hydroxy or trifluoromethyl groups or lower alkyl, alkoxy or aralkoxy groups, it also being possible that two adjacent radicals form an alkylene-dioxy radical, and $R_5$ represents a hydrogen or halogen atom, a hydroxy, trifluoromethyl or nitro group or a lower alkyl, alkoxy or aralkoxy radical, and their salts with acids (active substance A) together with 7-chloro-1-methyl-5-phenyl-1H-1,5-benzodiazepine-2,4 (3H,5H)-dione (active substance B), and their use as antidepressive agent.

2 Claims, No Drawings

MEDICINAL COMPOSITION AND ITS USE AS ANTIDEPRESSIVE AGENT

The invention relates to pharmaceutical combination compositions which contain an antidepressive compound of the general formula I

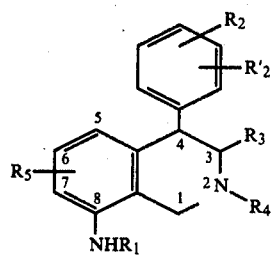

in which $R_1$, $R_3$ and $R_4$, which may be identical or different, and represent hydrogen atoms or lower alkyl or aralkyl groups, and $R_2$ and $R_2'$, which may be identical or different, represent hydrogen or halogen atoms, hydroxy or trifluoromethyl groups or lower alkyl, alkoxy or aralkoxy groups, it also being possible that two adjacent radicals form an alkylene-dioxy radical, and $R_5$ represents a hydrogen or halogen atom, a hydroxy, trifluoromethyl or nitro group or a lower alkyl, alkoxy or aralkoxy radical, and their salts with acids (active substance A) together with 7-chloro-1-methyl-5-phenyl-1H-1,5-benzodiazepine-2,4 (3H,5H)-dione (active substance B).

The compounds of the general formula I which may be used as active substance A are known from U.S. Pat. No. 3,577,424. Those compounds are preferred in which $R_2$ stands for the 4-hydroxy group, a 4-bromine atom or $R_2$ and $R_2'$ stand for a chlorine atom in the 3- and 4-position. Of particularly great importance is the compound of the formula I in which $R_1$, $R_2$, $R_2'$, $R_3$ and $R_5$ represent hydrogen and $R_4$ represents a methyl group. This compound is described in U.S. Pat. No. 3,577,424 and known under the name "Nomifensin" (INN). Nomifensin is used in the form of the hydrogeno-maleinate as a medicament for the treatment of depressive conditions. It is the first strongly active antidepressive agent which is not derived from a tricyclic ring system. In contradistinction to the known tricyclic antidepressive agents, Nomifensin does not entail serious side effects, cf. for example "Arzneimittelforschung" 23 (1973) 45–50.

In the case of depressions which are accompanied by marked anxiety conditions, it has proved favorable to carry out an accompanying therapy with a distinctly anxiolytically active preparation in addition to the basic medication with Nomifensin.

For the anxiolytic accompanying therapy, 7-chloro-1-methyl-5-phenyl-1H-1,5-benzodiazepin-2,4 (3H,5H)-dione has proved useful and has become known under the name Clobazam (INN) (cf. for example La Chimica e l'Industria 51, 479–483 (1969).

Now, it has been found advantageous to combine the two active substances A and B in one pharmaceutical composition. The use of such combined compositions not only simplifies the medication, but moreover it has also been found that, surprisingly, often smaller quantities of the combined active substances are required for the same result of the therapy than with separate medication.

The active substance A is a basic compound which is used in most cases in the form of a physiologically tolerated salt. For such salts there may be used the following acids, for example, hydrochloric acid, hydrobromic acid and hydriodic acid, phosphoric acid, sulfuric acid, amidosulfonic acid, methylsulfonic acid, nitric acid, formic acid, acetic acid, propionic acid, succinic acid tartaric acid, lactic acid, malonic acid, fumaric acid, citric acid, malic acid, mucic acid, benzoic acid, salicylic acid, aceturic acid, embonic acid, naphthalene-1,5-disulfonic acid, ascorbic acid, hydroxyethane-sulfonic acid, benzenesulfonic acid or also synthetic resins which contain basic groups.

The active substance B is a neutral compound which is sparingly soluble in water. Clobazam is, therefore, advantageously used in micronized form.

The combinations of active substances of the invention may be used in the forms which are usual for therapeutical treatment, for example in the form of tablets, powders, capsules, suppositories or dragées. Capsules, tablets and dragées are preferably used. The usual pharmaceutical auxiliaries, for example inert diluents and binders such as lactose, micro-crystalline cellulose, calcium carbonate, di-and tri-calcium phosphate, polyethylene glycol 4000–6000, gelatin, starch slime, disintegrating agents such as starches, ultra-amylopectin, cellulose and cellulose derivatives, aerosil, lubricants such as talcum, magnesium stearate, calcium stearate, stearic acid, may be added.

As tablets, there may also be used those which consist of several layers. They are prepared, for example by mixing the active substances with the pharmaceutical auxiliaries according the usual galenic methods of manufacture.

Dragées may be obtained, for example, by coating kernels with the agents used usually for dragée coatings, for example cane sugar, gelatin, gum arabic, talcum, calcium carbonate, cera carnauba, aerosil.

The preparation of capsules is likewise effected in known manner by mixing inert carriers such as maize starch, talcum, aerosil; gelatin capsules are preferably used.

The combination of the invention may also be supplied in the form of suppositories, which contain the usual carrier agents such as triglycerides of saturated fatty acids, or hydrogenated vegetable fats.

The preferred form of administration of the pharmaceutical preparations having an antidepressive action according to the invention is oral administration. The active substance A may be used in a dose of 5 to 50 mg per administration unit. Clobazam, the active substance B, is used in an amount of from 2 to 25 mg. In cases which require a higher dosage, a corresponding multiple of the mentioned dosages may be administered.

EXAMPLES:

| Capsules | | | |
|---|---|---|---|
| 1. | Nomifensin-hydrogen-maleinate | 50 mg | 25 mg |
| 2. | Clobazam | 15 mg | 7.5 mg |
| 3. | Corn starch | 35 mg | 17.5 mg |
| 4. | Micro-crystalline cellulose | 80 mg | 40 mg |
| 5. | Talcum | 10 mg | 5 mg |
| 6. | Highly disperse silicium dioxide | 6 mg | 3 mg |
| 7. | Magnesium stearate | 4 mg | 2 mg |

-continued

| Capsules | | |
|---|---|---|
| | 200 mg | 100 mg |

The micronized active substances 1 and 2 are mixed with the additives 3–7 The mixture is filled in known manner into hard gelatin capsules.

| Tablets | | | |
|---|---|---|---|
| 1. | Nomifensin | 25 mg | 50 mg |
| 2. | Clobazam | 7.5 mg | 15 mg |
| 3. | Lactose | 40 mg | 80 mg |
| 4. | Corn starch | 24 mg | 48 mg |
| 5. | Micro-crystalline cellulose | 20 mg | 40 mg |
| 6. | Highly disperse dioxide silicon | 3 mg | 6 mg |
| 7. | Polyvinyl pyrrolidine K25 | 6.5 mg | 13 mg |
| 8. | Talcum | 3.5 mg | 7 mg |
| 9. | Magnesium stearate | 0.5 mg | 1 mg |
| | | 130.0 mg | 260 mg |

The mixture for tablets from substances 1–9 is granulated and pressed into biconvex tablets.

Film lacquer tablets

The tablets are coated with one of the usual film lacquers.

Dragées

The granulate prepared for the preparation of tablets is pressed to dragée kernels. The dragée kernels are coated in known manner.

We claim:

1. A medicinal composition for the treatment of depression comprising, in combination, 2 to 25 parts by weight of 7-chloro-1-methyl-5-phenyl-1H-1,5-benzodiazepine-2,4(3H,5H)-dione together with 5 to 50 parts by weight of a compound of the formula

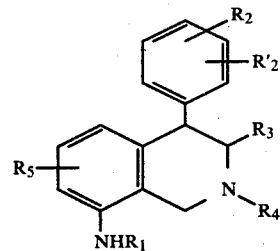

or a salt thereof with an acid, wherein $R_2 R_3$, and $R_4$, taken alone, may be the same or different, and are hydrogen, or lower alkyl or aralkyl; $R_2$ and $R_2'$, taken alone, may be the same or different, and are hydrogen, halogen, hydroxy, trifluoromethyl, lower alkyl, alkoxy, or aralkoxy; or two adjacent substituents, taken together, may be alkylene dioxy; and $R_5$ is hydrogen, halogen, hydroxy, trifluoromethyl, nitro, or lower alkyl, alkoxy, or aralkoxy.

2. The method of treating depression in a patient suffering therefrom which comprises administering to said patient an anti-depressively effective amount of medicinal composition as in claim 1.

* * * * *

UNITED STATES PATENT AND TRADEMARK OFFICE
CERTIFICATE OF CORRECTION

PATENT NO. : 4,189,478
DATED : 02/19/80
INVENTOR(S) : Schmitt et al.

It is certified that error appears in the above-identified patent and that said Letters Patent is hereby corrected as shown below:

In Claim 1, line 7 (the first line under the structural formula), change "$R_2$" to --$R_1$,--.

Signed and Sealed this

Twenty-third Day of April 1985

[SEAL]

Attest:

DONALD J. QUIGG

*Attesting Officer*   *Acting Commissioner of Patents and Trademarks*